(12) United States Patent
Steingisser et al.

(10) Patent No.: US 10,271,873 B2
(45) Date of Patent: Apr. 30, 2019

(54) SHEATHLESS GUIDE CATHETER ASSEMBLY

(71) Applicant: Medtronic Vascular, Inc., Santa Rosa, CA (US)

(72) Inventors: H. Allan Steingisser, Santa Rosa, CA (US); William Berthiaume, Santa Rosa, CA (US); Joseph Berglund, Santa Rosa, CA (US); Conor Flannery, Oakland, CA (US); Maria Valdovinos, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 253 days.

(21) Appl. No.: 14/922,355

(22) Filed: Oct. 26, 2015

(65) Prior Publication Data
US 2017/0113023 A1 Apr. 27, 2017

(51) Int. Cl.
*A61B 17/34* (2006.01)
*A61M 25/06* (2006.01)
(Continued)

(52) U.S. Cl.
CPC ......... *A61B 17/34* (2013.01); *A61M 25/0068* (2013.01); *A61M 25/0102* (2013.01);
(Continued)

(58) Field of Classification Search
CPC .... A61M 2025/0681; A61M 25/09041; A61M 2025/0183; A61M 2025/018
See application file for complete search history.

(56) References Cited

U.S. PATENT DOCUMENTS 5,364,376 A * 11/1994 Horzewski ........ A61M 25/0172
604/247
5,496,344 A 3/1996 Kanesaka et al.
(Continued)

FOREIGN PATENT DOCUMENTS

WO WO2005/011788 2/2005
WO WO2007/067545 6/2007
WO WO2015/031252 3/2015

OTHER PUBLICATIONS

PCT/US2016/058707, The International Search Report and the Written Opinion of the International Searching Authority, dated Feb. 3, 2017.

*Primary Examiner* — Nathan R Price
*Assistant Examiner* — Tasnim Mehjabin Ahmed
(74) *Attorney, Agent, or Firm* — Medler Ferro Woodhouse & Mills PLLC

(57) ABSTRACT

A guide catheter assembly includes a dilator and a guide catheter. The dilator includes a dilator lumen extending from a distal opening at a distal end to a proximal opening at a proximal end, and a side exit port proximal of the distal opening and in communication with the dilator lumen. The guide catheter includes a proximal end, a distal end, and a guide lumen extending therebetween. The dilator and the guide lumen are sized such that the dilator can pass through the guide lumen. The dilator and the guide catheter are sized such that with the proximal end of the dilator generally aligned along an axis with the proximal end of the guide catheter, the distal end of the dilator extends distally past the distal end of the guide catheter and the side exit port is disposed distal of the distal end of the guide catheter.

11 Claims, 13 Drawing Sheets

(51) Int. Cl.
*A61M 25/09* (2006.01)
*A61M 29/00* (2006.01)
*A61M 25/00* (2006.01)
*A61M 25/01* (2006.01)

(52) U.S. Cl.
CPC ........ *A61M 25/0662* (2013.01); *A61M 25/09* (2013.01); *A61M 29/00* (2013.01); A61M 2025/0079 (2013.01); A61M 2025/018 (2013.01)

(56) References Cited

U.S. PATENT DOCUMENTS

| | | | |
|---|---|---|---|
| 5,976,107 A * | 11/1999 | Mertens | A61M 25/104 604/164.13 |
| 6,006,114 A | 12/1999 | Seppanen et al. | |
| 6,562,049 B1 * | 5/2003 | Norlander | A61M 25/003 606/108 |
| 2007/0185521 A1 * | 8/2007 | Bui | A61M 25/0662 606/191 |
| 2008/0275395 A1 * | 11/2008 | Asbury | A61L 29/06 604/113 |
| 2009/0192584 A1 * | 7/2009 | Gerdts | A61F 2/95 623/1.11 |
| 2010/0312223 A1 * | 12/2010 | Kozak | A61B 17/32037 604/528 |
| 2015/0133865 A1 * | 5/2015 | Okamura | A61M 25/0662 604/164.1 |

* cited by examiner

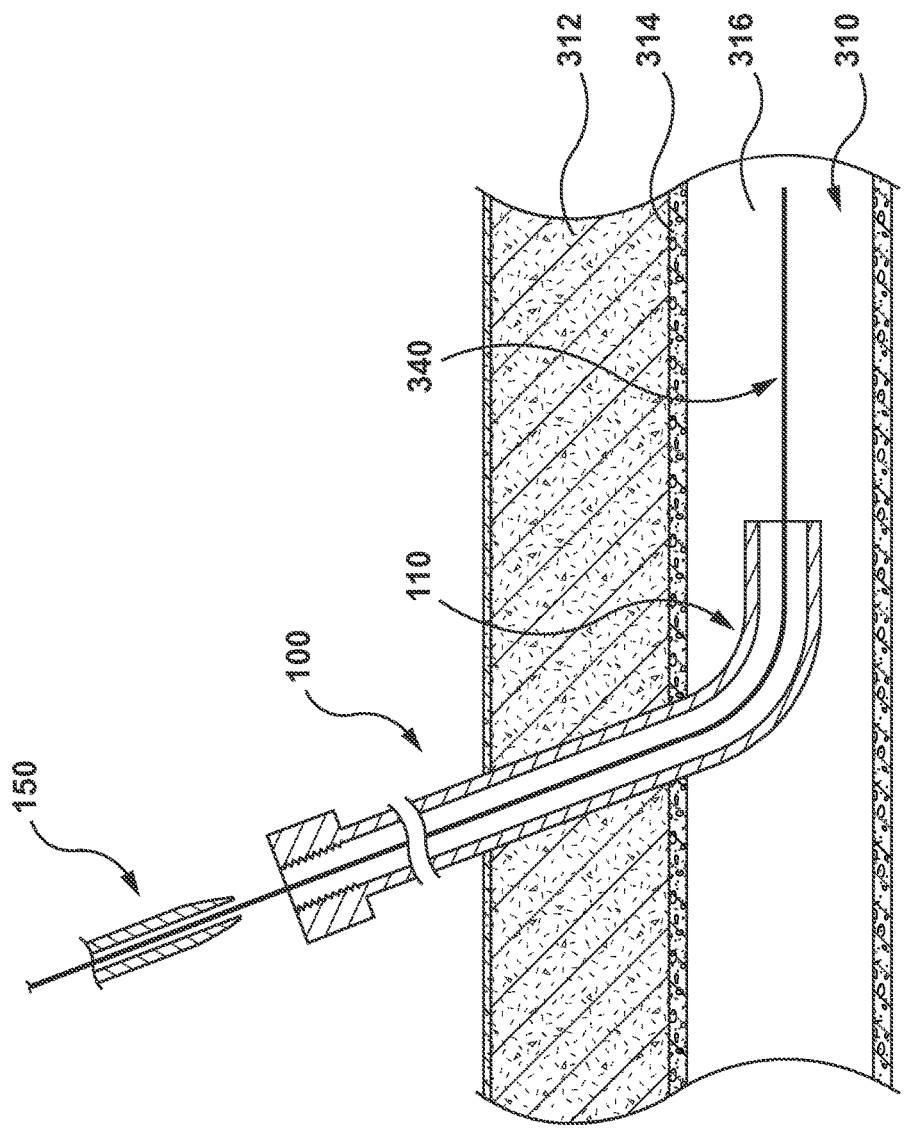

SHEATHLESS GUIDE CATHETER ASSEMBLY

FIELD OF THE INVENTION

Embodiments hereof relate to sheathless guide catheter assemblies and methods of using such sheathless guide catheter assemblies.

BACKGROUND OF THE INVENTION

Percutaneous transluminal catheterization procedures such as angioplasty, stent implantation, stent-graft implantation, and other prosthesis implantations require minimally invasive access to a patient's vasculature. Generally access is into an artery such as the common femoral artery using the Seldinger technique. A guide catheter is then advanced over a guidewire to a desired site in the vasculature near a treatment site. Procedural devices may then be advanced through the guide catheter to the treatment site.

The process for gaining repeated access to the vessel can include several steps with a hollow needle, medical guidewires, guidewire exchanges, introducer sheaths, and exchanges thereof. Such steps may cause trauma to the vessel. While using an introducer sheath typically reduces tissue damage from catheter exchanges therethrough, the sheath requires a larger puncture/access opening, which takes longer to close after the procedure. So-called "sheathless" procedures have been introduced which use smaller diameter introducer sheaths. However, sheaths are still used, which require additional exchanges and can cause trauma to the access site of the vessel.

Accordingly, there is a need for devices and methods for guide catheter access to a vessel which reduce the number of steps to access the vessel and reduce trauma to the vessel at the access site.

BRIEF SUMMARY OF THE INVENTION

Embodiments hereof are directed to a guide catheter assembly including a dilator and a guide catheter. The dilator includes a proximal end, a distal end, a dilator lumen extending from a distal opening at the distal end to a proximal opening at the proximal end, and a side exit port proximal of the distal opening. The side exit port is in communication with the dilator lumen. The guide catheter includes a proximal end, a distal end, and a guide lumen extending between the proximal and distal ends of the guide catheter. The dilator and the guide lumen are sized such that the dilator can pass through the guide lumen. The lengths of the dilator and the guide catheter are sized such that with the proximal end of the dilator generally aligned along an axis with the proximal end of the guide catheter, the distal end of the dilator extends distally past the distal end of the guide catheter and the side exit port is disposed distal of the distal end of the guide catheter.

Embodiments hereof are also directed to a guide catheter assembly including a guide catheter and a dilator. The dilator includes a proximal end, a distal end, and a dilator lumen extending from a distal opening at the distal end to a side exit port proximal of the distal opening. The dilator includes a tapered distal portion adjacent the distal end. The guide catheter includes a proximal end, a distal end, and a guide lumen extending between the proximal end and the distal end of the guide catheter. The dilator and the guide lumen are sized such that the dilator can pass through the guide lumen. The lengths of the dilator and guide catheter are sized such that with the proximal end of the dilator generally aligned along an axis with the proximal end of the guide catheter, the distal end of the dilator extends distally past the distal end of the guide catheter and the side exit port is disposed distal of the distal end of the guide catheter.

Embodiments hereof are also directed to a method for accessing a vessel and delivering a guide catheter to a desired location in the vasculature of a patient. The method includes inserting a needle through a wall of the vessel at an access site to create an access opening, wherein the needle includes a needle lumen. A first wire is inserted through the needle lumen and into the vessel. The first wire has a first diameter. The needle is then removed from the vessel over the first wire, thereby leaving a distal end of the first wire in a lumen of the vessel with the first wire extending through the access opening. A proximal end of the first wire is inserted into a distal opening of a dilator of a guide catheter assembly and into a dilator lumen of the dilator, wherein the guide catheter assembly includes the dilator and a guide catheter having a guide lumen sized to receive the dilator therein. The proximal end of the first wire is guided out of a side exit port of the dilator. The side exit port is located proximal of the distal opening and distal of a distal end the guide catheter when a proximal end of the dilator and a proximal end of guide catheter are generally aligned along an axis. The guide catheter assembly is advanced over the first wire until a distal portion of the dilator enters the vessel. The first wire is removed from the vessel and the dilator by pulling the proximal end of the first wire such that the first wire retracts from the vessel, through the distal opening, and out of the side exit port. A second guidewire is inserted into a proximal opening at a proximal end of the dilator, through the dilator lumen, and out of the distal opening into the vessel. The guide catheter assembly is advanced over the second guidewire until a distal portion of the guide catheter is disposed in the lumen of the vessel. The dilator may be withdrawn through the guide lumen after the distal portion of the guide catheter is disposed in the vessel.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 5-13 illustrate a method of accessing a vessel with the guide catheter assembly of FIG. 1.

DETAILED DESCRIPTION OF THE INVENTION

Specific embodiments of the present invention are now described with reference to the figures, wherein like reference numbers indicate identical or functionally similar elements. The terms "distal" and "proximal" when used in the following description to refer to a catheter or dilator are with respect to a position or direction relative to the treating clinician. Thus, "distal" and "distally" refer to positions distant from or in a direction away from the clinician and "proximal" and "proximally" refer to positions near or in a direction toward the clinician.

Figure 1:
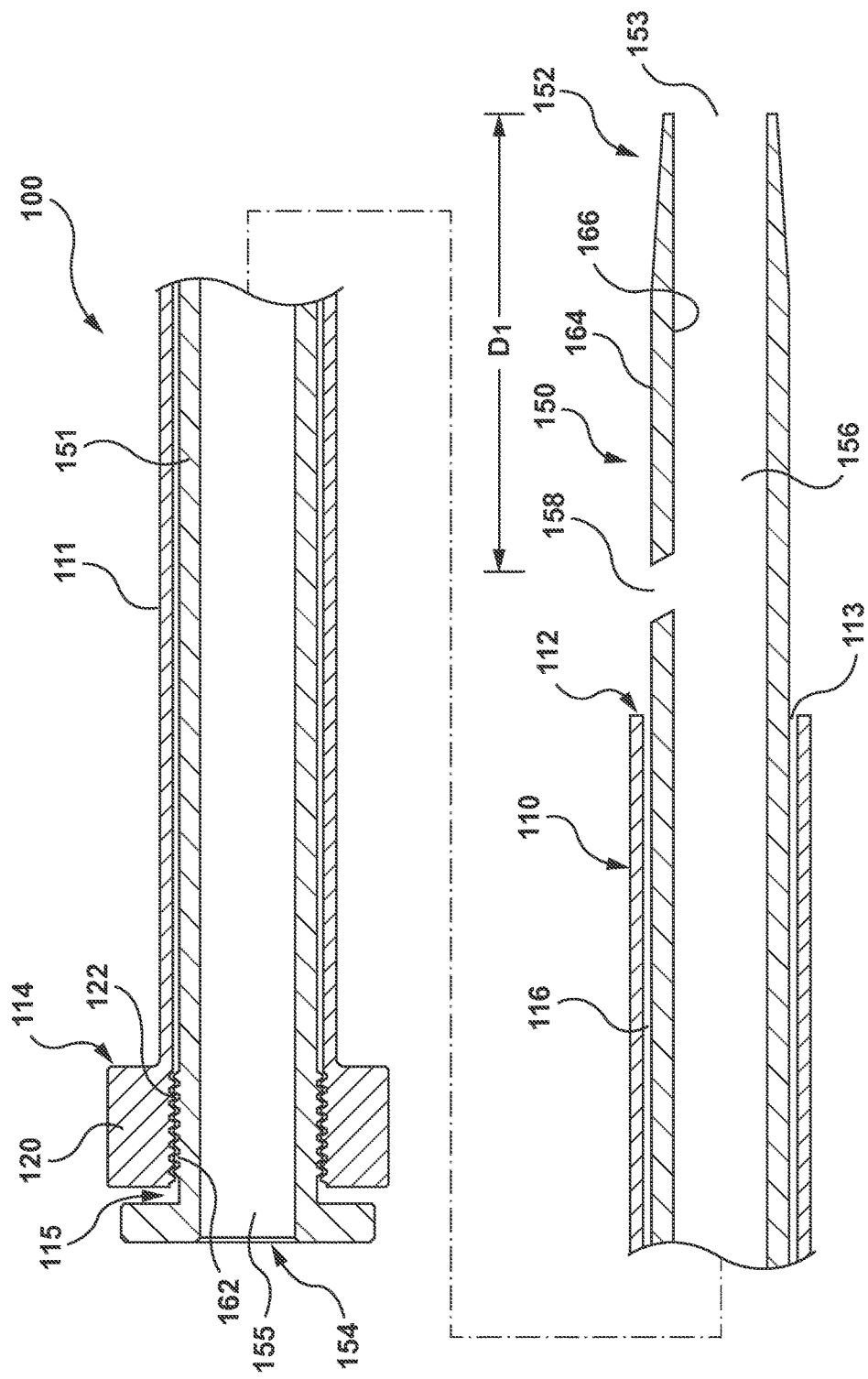
FIG. 1 is a broken longitudinal cross-section of a guide catheter assembly according to an embodiment hereof.

FIG. 1 shows a guide catheter assembly 100 according to an embodiment hereof. Guide catheter assembly 100 includes a guide catheter 110 and a dilator 150. Guide catheter 110 includes a generally tubular guide shaft 111 including a distal end 112, a proximal end 114, and a guide lumen 116 extending through guide shaft 111. Guide lumen 116 extends from a proximal opening 115 at proximal end 114 to a distal opening 113 at distal end 112. Guide lumen 116 is sized such that dilator 150 can be removably disposed therethrough, as explained in more detail below. Guide catheters 110 are commonly available in a range of sizes, e.g. outer diameters, which are labeled according to the French gauge system, and the guide lumens 116 range in size correspondingly. For example only, a 5F guide catheter 110 is available from at least one manufacturer with a guide lumen 116 measuring 0.058 inch. Similarly, a 6F guide catheter 110 is available from at least one manufacturer with a guide lumen 116 measuring 0.071 inch. A 7F guide catheter 110 is available from at least one manufacturer with a guide lumen 116 measuring 0.081 inch. An 8F guide catheter 110 is available from at least one manufacturer with a guide lumen 116 measuring 0.090 inch.

Guide catheter 110 may be substantially straight, or guide catheter 110 may include a curve (not shown) proximate the distal region of guide catheter 110. Any one of a number of pre-formed curve shapes may be incorporated into guide catheter 110, such as Judkins-type or Amplatz-type curves, as non-limiting examples. Such a curve may be pre-formed utilizing various known methods including, but not limited to, the method disclosed in U.S. Pat. No. 5,902,287 entitled "Guiding Catheter and Method of Making Same." A desired curve may be manually created from a straight or pre-formed distal region of guide catheter 110 by manipulation of one or more steering wires, as known in the art.

In the embodiment shown, guide catheter 110 includes a hub 120 at proximal end 114. However, hub 120 may be a separate piece coupled to guide shaft 111 of guide catheter 110. In the embodiment shown an inner surface of guide shaft 111 at proximal end 114 includes threads 122 which are configured to mate with threads 162 on an outer surface of dilator 150, as explained in more detail below. Guide catheter 110 and/or hub 120 may include other features, such as, but not limited to, steering mechanisms, additional lumens, etc.

Guide shaft 111 may be constructed from any suitable materials known to those of ordinary skill in the field of guide catheters. Material examples include, but are not limited to polyethylene (PE), polyurethane, and polyethylene block amide copolymer (PEBA). Guide catheters commonly include inner and outer polymer layers with a reinforcement layer interposed therebetween.

Dilator 150 includes a generally tubular dilator shaft 151 including a distal end 152, a proximal end 154, and a dilator lumen 156 extending through dilator shaft 151. Dilator 150 may also be referred to as a leader or a flexible leader, especially where the intended method of use is to leave the dilator extending distally from the guide catheter while the assembly is navigated through the patient's vasculature. Dilator lumen 156 extends from a proximal opening 155 at proximal end 154 to a distal opening 153 at distal end 152. Dilator lumen 156 is sized such that a guidewire may be disposed therethrough, as explained in more detail below. Further, dilator shaft 151 is sized such that an outer diameter of dilator shaft 151 may have a close sliding fit within guide lumen 116. In an embodiment dilator lumen 156 is sized to receive a nominal 0.035 or 0.038 inch guidewire. The term "nominal" as used herein means that the guidewire is referred to in the industry by the diameter named (in this case, 0.035 or 0.038 inch). However, the actual diameter of the guidewire may vary up to 10% of the nominal size. In an embodiment, dilator lumen 156 has a diameter in the range of 0.015-0.040 inch.

Dilator 150 is longer than guide catheter 110 such that dilator 150 is configured to protrude from distal opening 113 of guide catheter 110. As can be seen in FIG. 1, with proximal end 154 of dilator 150 generally aligned along an axis with proximal end 114 of guide catheter 110, distal end 152 of dilator 150 extends distally beyond distal end 112 of guide catheter 112. The term "generally aligned along an axis" as used herein means that the proximal end 154 of dilator 150 is positioned on a common axis at or proximal to the same location as the proximal end 114 of guide catheter 110.

Dilator 150 also includes a side exit port 158, as shown in FIG. 1. Side exit port 158 is an opening through dilator shaft 151 from an outer surface 164 of dilator shaft 151 through an inner surface 166 of dilator shaft 151. Thus, side exit port 158 may also be referred to as a through-hole and provides a passageway for fluid communication or device movement between the outside of dilator shaft 151 to dilator lumen 156. Side exit port 158 is located between proximal opening 155 and distal opening 153. More particularly, with dilator 150 disposed through guide lumen 116 of guide catheter 110 and with proximal end 154 of dilator 150 generally aligned along an axis with proximal end 114 of guide catheter 110, as explained above, side exit port 158 is disposed between distal opening 153 of dilator 150 and distal opening 113 of guide catheter 110. A distance D1 from distal opening 153 to side exit port 158 is sufficient such that, when distal end 152 is disposed in a vessel of a patient's vasculature, side exit port 158 remains outside of the patient's body. Commercial guide catheters are available in a range of lengths, beginning as short as 30 cm, but typically measuring between 90-150 cm long. In an embodiment, distance D1 is in the range of 0.5-12 inches. Side exit port 158 is sized to receive what is known in the art as a short wire, which is so-named because it does not need to be the full length of a guidewire used for advancing the guide catheter assembly to the desired site. In an embodiment, such a short wire is a nominally 0.018 to 0.021 inch diameter guidewire. Thus, side exit port 158 in such an embodiment is sized to receive a nominal 0.018 to 0.021 inch guidewire.

Dilator 150 may include features for removably coupling dilator 150 to guide catheter 110. In the embodiment of FIG. 1, dilator shaft 151 includes threads 162 at proximal end 154 which mate with threads 122 on an inner surface of guide catheter 150. Other ways to removably couple dilator 150 to guide catheter 110 may be used instead, such as, but not limited to a luer lock or luer slip fitting, a radial protrusion on one component and a mating indentation on the other component, or an external cap on dilator end 154 that press-fits over guide catheter hub 120. However, such features to removably couple dilator 150 to guide catheter 110 need not be included.

Figure 2:
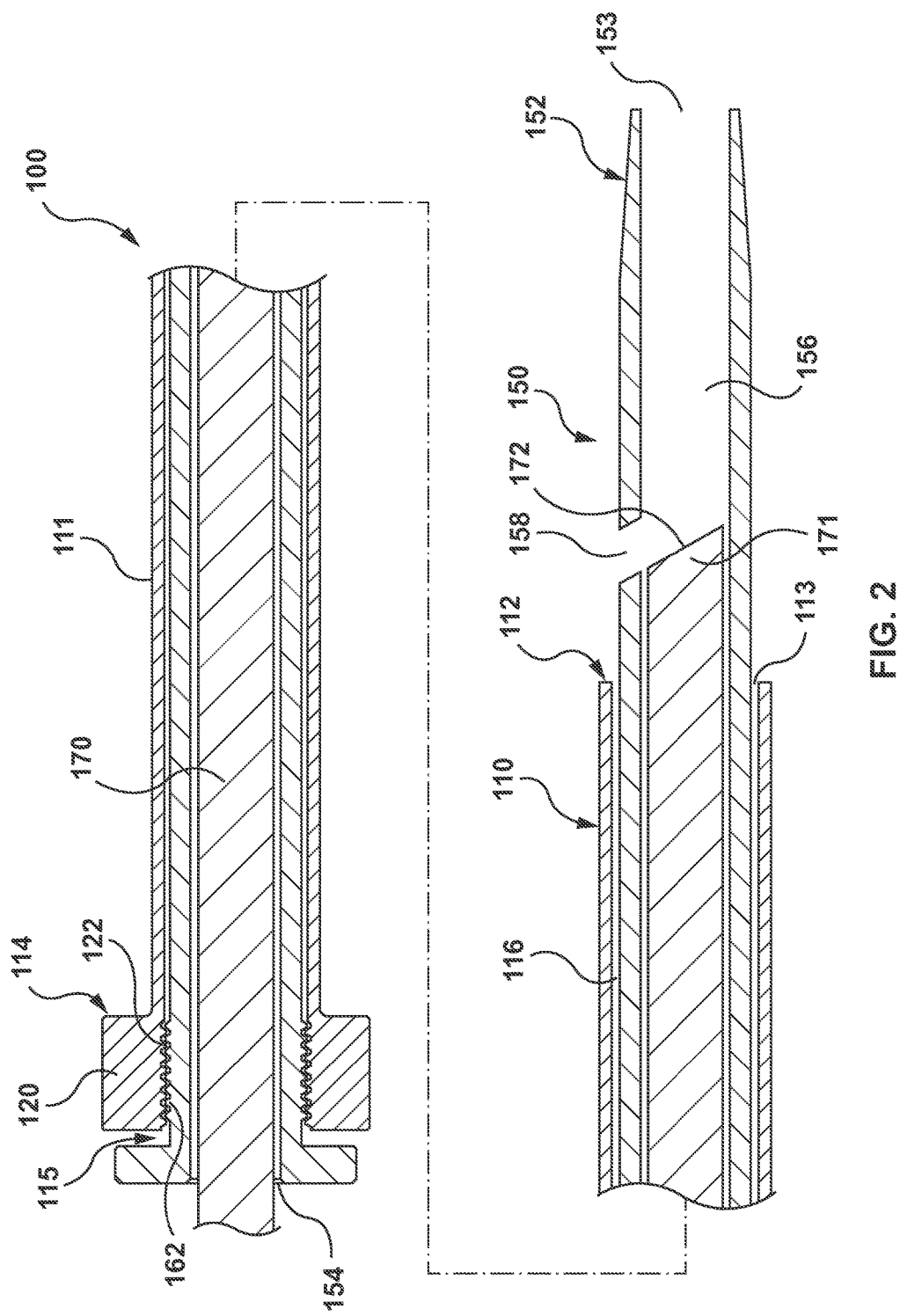
FIG. 2 is a broken longitudinal cross-section of the guide catheter assembly of FIG. 1 with an optional obturator shown.

FIG. 2 shows an optional feature that may be included as part of guide catheter assembly 100. The reference numerals used in FIG. 2 for features in common with FIG. 1 are the same as in FIG. 1 because the features are the same. FIG. 2 additionally shows an obturator 170 disposed through dilator lumen 156. Obturator 170 may also be called a deflector, a stylet or a stiffening stylet. Obturator 170 is sized so as to be able to slidably fit within dilator lumen 156. Obturator 170 includes a proximal end (not shown) and a distal end 171. In the embodiment of FIG. 2, distal end 171 includes an angled surface 172. With obturator 170 disposed through dilator lumen 156 such that angled surface 172 is disposed proximally adjacent to side exit port 158, angled surface 172 almost completely obstructs dilator lumen 156 and deflects a guidewire towards side exit port 158 when such a guidewire is inserted through distal opening 153 and advanced proximally towards side exit port 158. Further, obturator 170 may stiffen guide catheter assembly 100 to straighten a pre-formed curve in guide catheter 110 and assist in advancing guide catheter assembly 100 through the vasculature. Obturator 170 may be made from materials commonly used for obturators, dilators or stylets, such as, but not limited to, polyethylene (PE), polypropylene (PP), fluorinated ethylene propylene (FEP), or stainless steel.

Figure 3:
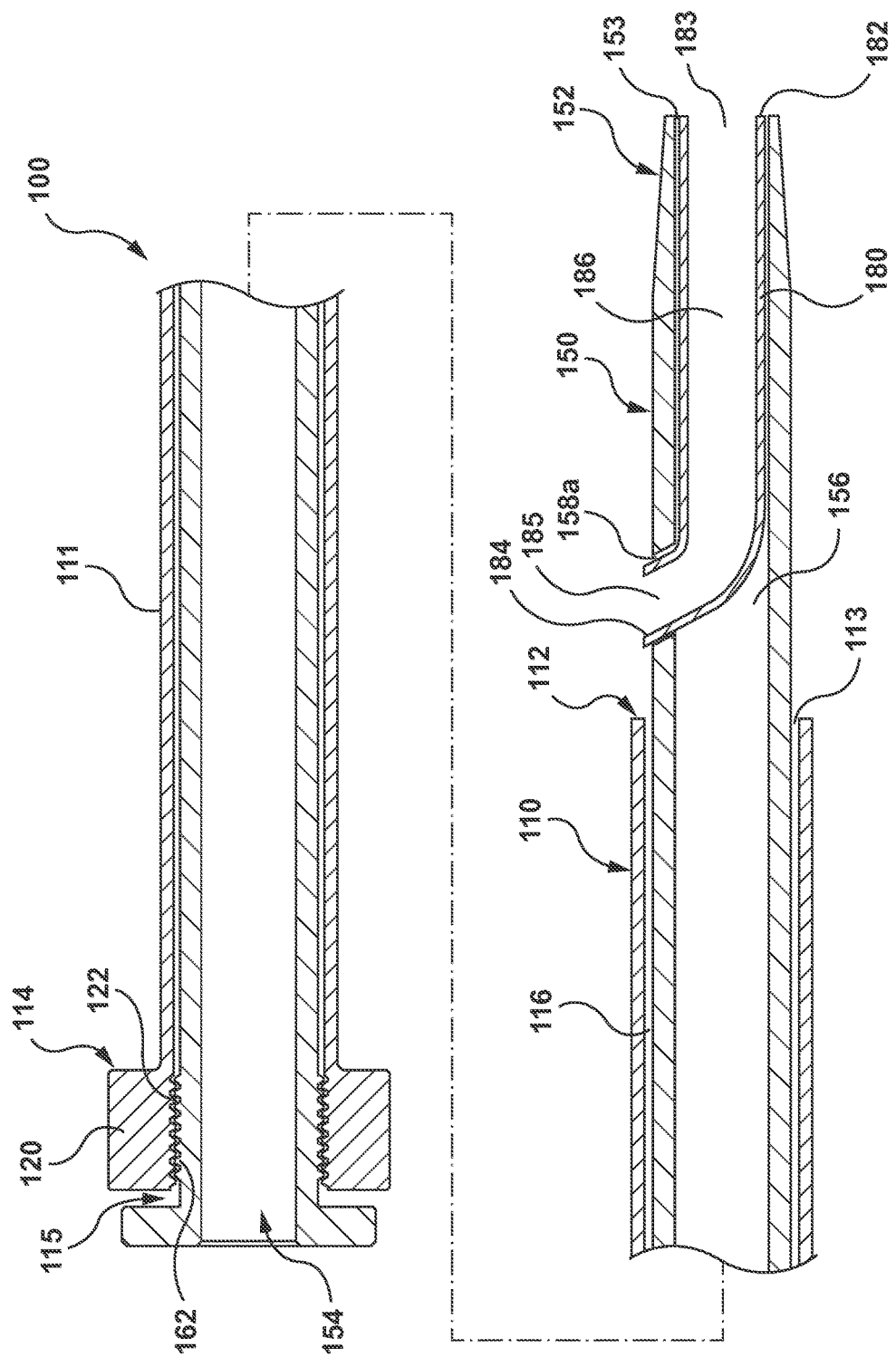
FIG. 3 is a broken longitudinal cross-section of the guide catheter assembly of FIG. 1 with an optional removable short wire tube shown.

FIG. 3 shows another optional feature that may be included as part of guide catheter assembly 100. The reference numerals used in FIG. 3 for features in common with FIG. 1 are the same as in FIG. 1 because the features are the same. FIG. 3 additionally shows a removable short wire tube 180 disposed through side exit port 158a, into dilator lumen 156, and extending to distal opening 153. Side exit port 158a in FIG. 3 may be larger than side exit port 158 in FIGS. 1-2 to accommodate short wire tube 180. However, side exit port 158 in FIGS. 1-2 may be the same size as side exit port 158a if such as size is large enough to accommodate short wire tube 180 and a "short wire," as described in more detail below.

Removable short wire tube 180 includes a distal end 182, a proximal end 184, and a tube lumen 186 extending from a distal opening 183 at distal end 182 to a proximal opening 185 at proximal end 184. When removable short wire tube 180 is in place as part of catheter assembly 100, distal end 182 is adjacent distal end 152 of dilator 150, proximal end 184 is disposed adjacent side exit port 158a, and removable short wire tube 180 extends through a distal portion of dilator lumen 156 from distal opening 153 through side exit port 158a. In use, as described in more detail below, a "short wire" with a nominal diameter of 0.018-0.021 inch is inserted through distal opening 183, and removable short wire tube 180 guides the short wire through tube lumen 186, out of side exit port 158a and proximal opening 185. After guide catheter assembly 100 is advanced over the short wire, as described in more detail below, the short wire is removed by pulling the short wire from where the short wire exits proximal opening 185. Removable tube 180 can be removed from dilator lumen 156 simultaneously with or after the removal of the short wire by pulling on proximal end 184. A guidewire with a larger diameter than the short wire can then be advanced through dilator lumen 156 from proximal opening 154 to distal opening 153. Removable short wire tube 180 assists in guiding the short wire to side exit port 158a, and tube lumen 186 more closely matches the diameter of the short wire because tube lumen 186 does not need to accommodate a larger guidewire, as does dilator lumen 156.

Removable short wire tube 180 may be made from materials commonly used in catheters, such as, but not limited to, any suitable material, such as, but not limited to, polyamide, polyethylene (PE), polyimide, fluorinated ethylene propylene (FEP), polytetrafluoroethylene (PTFE) or polyethylene block amide copolymer (PEBA). Short wire tube 180 may be made from biocompatible metals such as stainless steel or superelastic NiTi (nitinol) provided that sufficient flexibility is provided, as by a pattern of openings in the tubular wall, or by making tube 180 from a coiled wire. Combinations of the above polymeric and metallic materials are also possible.

Figure 4:
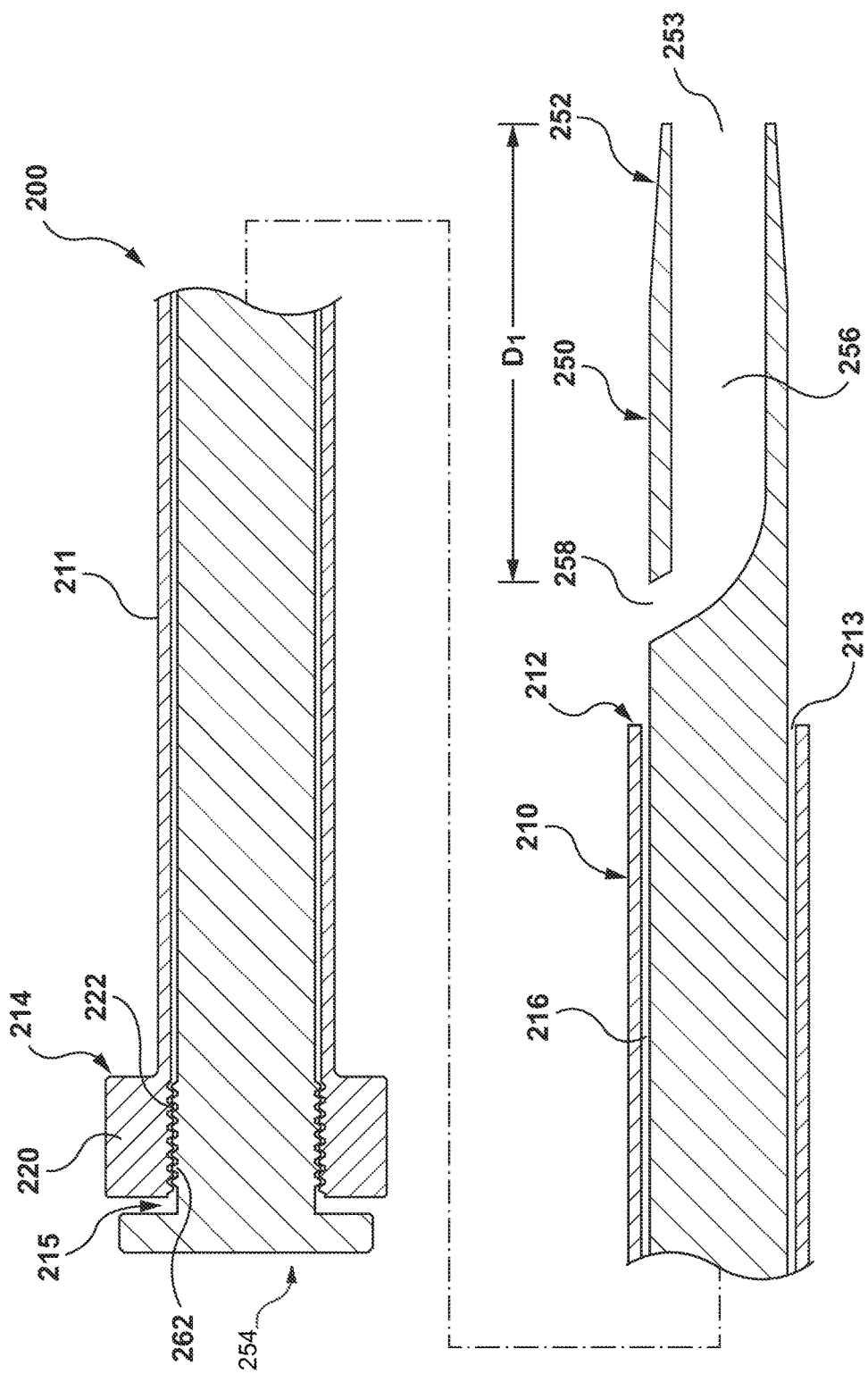
FIG. 4 is a broken longitudinal cross-section of a guide catheter assembly according to another embodiment hereof.

FIG. 4 shows a guide catheter assembly 200 according to another embodiment hereof. Guide catheter assembly 200 includes a guide catheter 210 and a dilator 250. Guide catheter 210 may be the same as guide catheter 110 of FIGS. 1-3, including a guide shaft 211 and a hub 220. Dilator 250 includes a generally tubular dilator shaft 251 including a distal end 252, a proximal end 254, and a dilator lumen 256. Dilator lumen 256 extends only from a distal opening 253 at distal end 252 to a side exit port 258. Thus, in contrast to the embodiments of FIGS. 1-3, dilator lumen 256 extends only through the portion of dilator 250 disposed distal of guide catheter distal end 212, as explained in more detail below. Dilator lumen 256 is sized such that a short wire may be disposed therethrough. Thus, in an embodiment, dilator lumen 256 is sized to receive a nominal 0.018 to 0.021 inch guidewire. Further, dilator shaft 251 is sized such that an outer diameter of dilator shaft 251 fits within guide lumen 216.

Dilator 250 is longer than guide catheter 210 such that with dilator 250 disposed through proximal opening 215 of guide catheter 210, dilator 250 is configured to protrude from distal opening 213 of guide catheter 210. As can be seen in FIG. 4, with proximal end 254 of dilator 250 generally aligned along an axis with proximal end 214 of guide catheter 210, distal end 252 of dilator 250 extends distally beyond distal end 212 of guide catheter 212.

Further, with dilator 250 disposed through guide lumen 216 of guide catheter 210 and with proximal end 254 of dilator 250 generally aligned along an axis with proximal end 214 of guide catheter 210, side exit port 258 is disposed between distal opening 253 of dilator 250 and distal opening 213 of guide catheter 210. As explained above with regard to the embodiment of FIG. 1, a distance D1 from distal opening 253 to side exit port 258 is sufficient such that with distal end 252 disposed in a vessel of a patient's vasculature, side exit port 258 remains outside of the patient's body. In an embodiment, distance D1 is in the range of 0.5-12 inches. Side exit port 258 is sized to receive a short wire, as will be explained in more detail below.

Dilator 250 may include features for removably coupling dilator 250 to guide catheter 210. In the embodiment of FIG. 4, dilator shaft 251 includes threads 262 at proximal end 254 which mate with threads 222 on an inner surface of guide catheter 250. Other ways to removably couple dilator 250 to guide catheter 210 may be used instead, as described above regarding the embodiment shown in FIG. 1.

FIGS. 5-13 illustrate an embodiment of a method for accessing the vasculature and advancing a guide catheter towards a desired site using guide catheter assembly 100 or guide catheter assembly 200 described above. FIGS. 5-13 show an embodiment of the method using guide catheter assembly 100 of FIG. 1. Where appropriate, differences in the method will be described with respect to use of the additional components of FIGS. 2-3 or guide catheter assembly 200 of FIG. 4.

Figure 5:
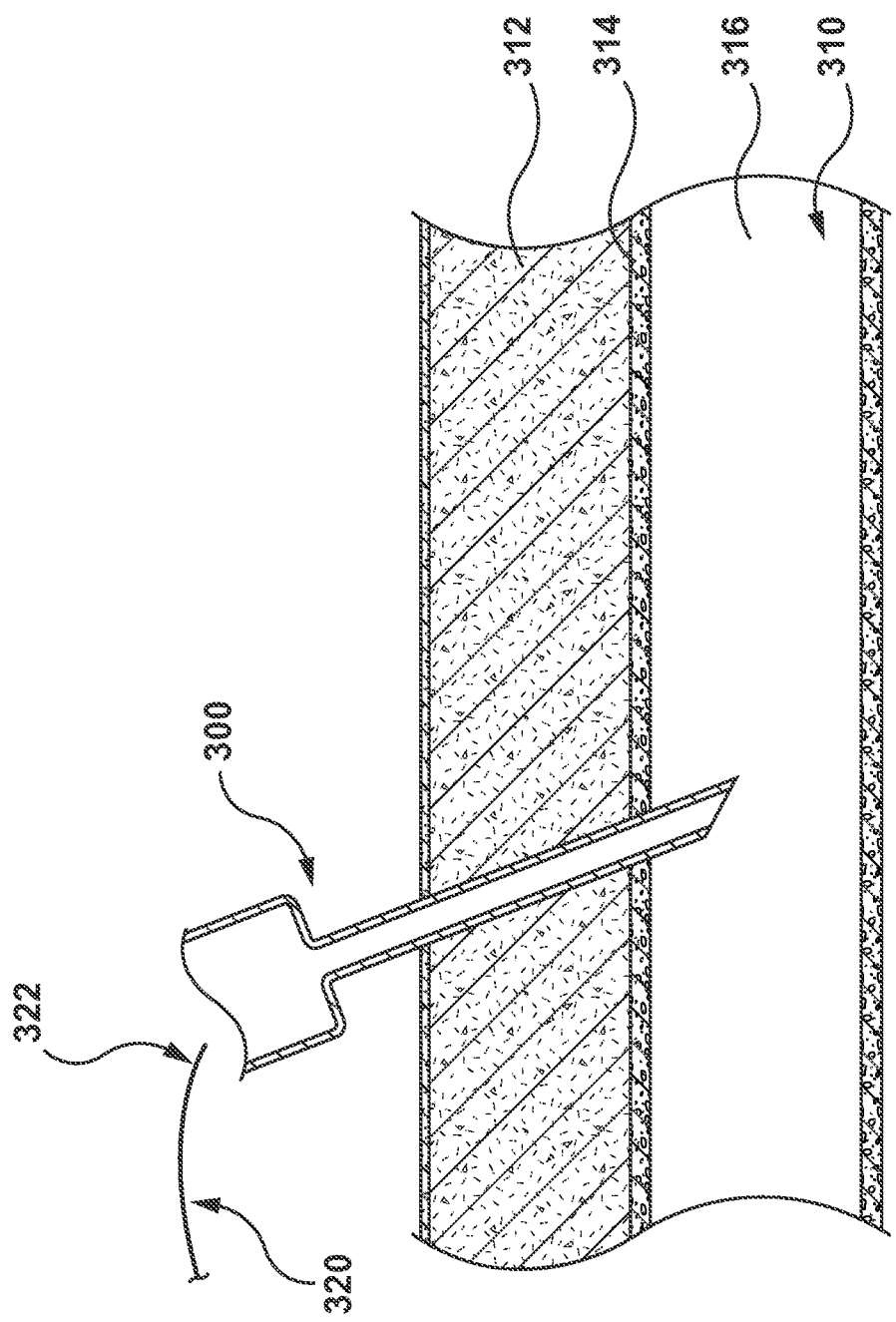

In a first step, a needle 300 is used to gain access to a vessel 310 of a patient's vasculature. Needle 300 is inserted through tissue 312, through wall 314 of vessel 310, and into lumen 316 of vessel 310, as shown in FIG. 5. In some cases, a shallow incision may first be made through the patient's skin into tissue 312. Vessel 310 can be any vessel to which a clinician wishes to gain access such that guide catheter assembly 100 may be advanced to a desired site. For example, and not by way of limitation, vessel 310 may be an arterial blood vessel such as a femoral artery, brachial artery, radial artery, or subclavian artery. Needle 300 may be any needle used to access a vessel, as is known in the art, but the size of needle 300 is selected to receive the desired short wire. For example, and not by way of limitation, needle 300 may be a 21 gauge angiographic needle, which size is used with a 0.018 inch short wire in the modified Seldinger percutaneous insertion technique.

With needle 300 having gained access to vessel 310, a short wire 320 is inserted through an opening in a proximal end of needle 300, as shown in FIG. 5. Short wire 320 may be a nominally 0.018-0.021 inch diameter guidewire, as known in the art. As described above, short wire 320 is referred to as a "short" wire as it does not need to be the full length of a guidewire used for advancing the guide catheter assembly to the desired site. Further, short wire 320 is generally smaller in diameter than the full length guidewire as short wire 320 is used with needle 300 and dilator 150, and it is desirable for needle 300 to have a small diameter as it is used during the first access to the vessel 310.

Figure 6:
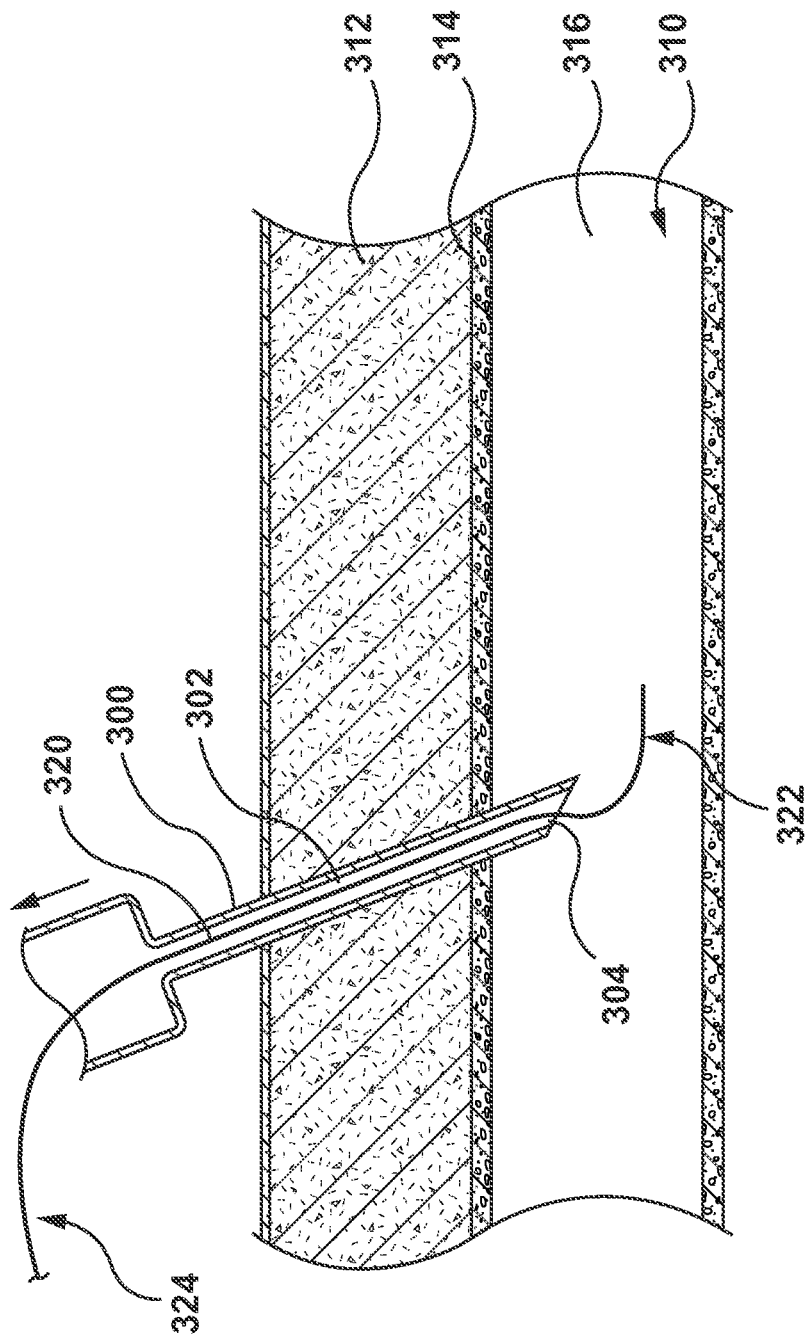

Short wire 320 is then advanced through a lumen 302 in needle 300 and out of a distal opening 304 of needle 300, as shown in FIG. 6. Thus, a distal end 322 of short wire 320 is disposed in lumen 316 and a proximal end 324 of short wire 320 is disposed outside of the patient and proximal to a proximal end of needle 300.

Figure 7:
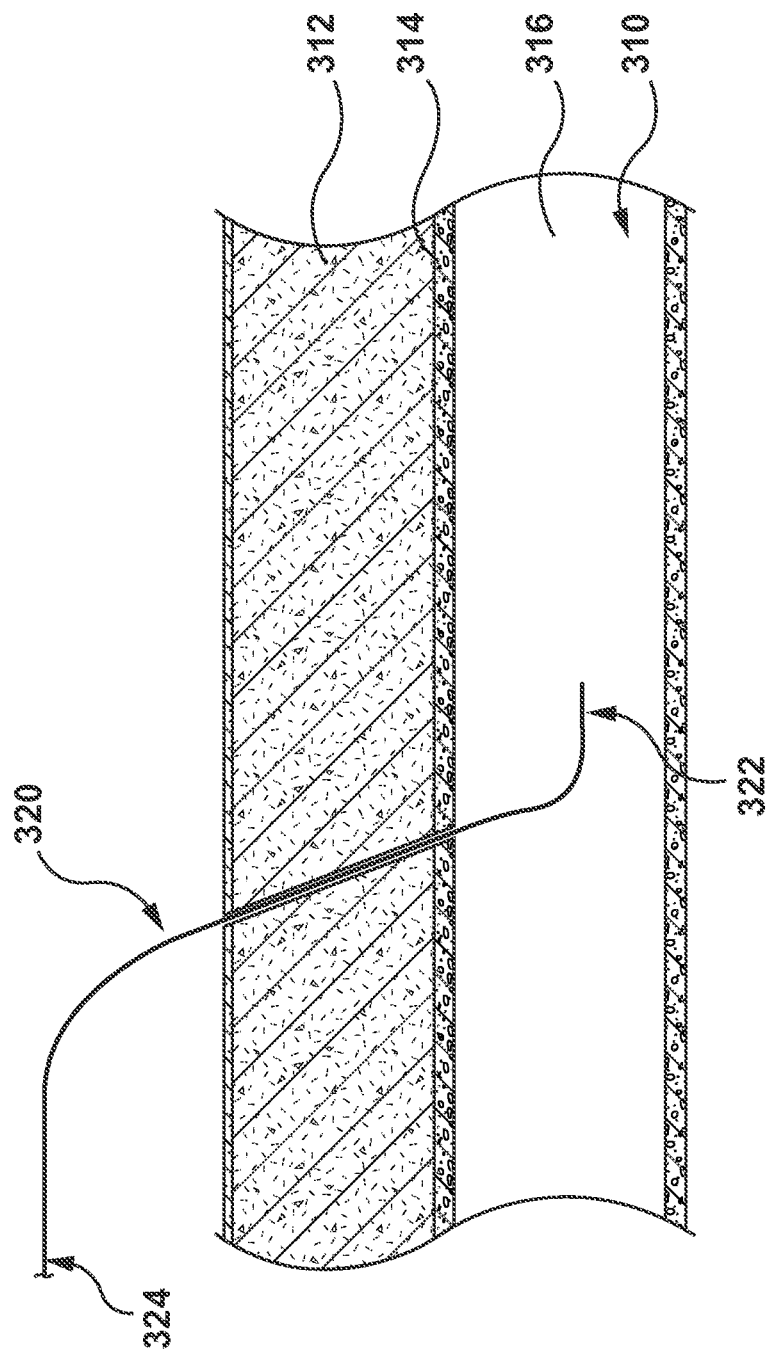

With short wire 320 disposed through needle 300 and into vessel 310, needle 300 may be withdrawn from vessel 310 by pulling needle 300 proximally over short wire 320, as indicated by the arrow in FIG. 6. This leaves short wire 320 with distal end 322 disposed in vessel 310 and proximal end 324 disposed outside of the body of the patient, as shown in FIG. 7.

Figure 8:
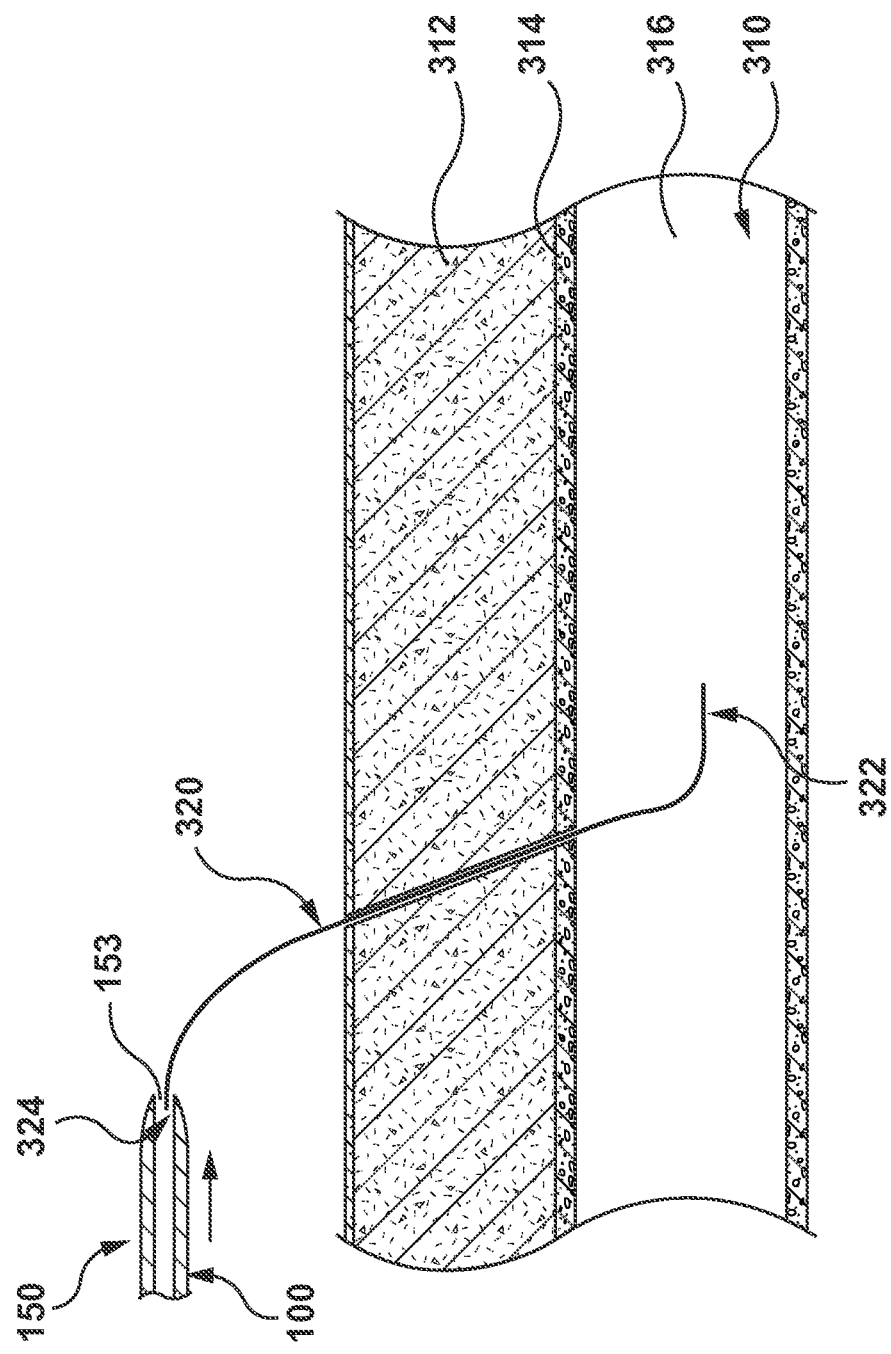

Proximal end 324 of short wire 320 is then loaded into guide catheter assembly 100, as shown in FIG. 8. Short wire 320 is loaded into guide catheter assembly 100 by inserting proximal end 324 of short wire 320 into distal opening 153 of dilator 150. If the guide catheter assembly of the embodiment of FIG. 3 is used, proximal end 324 of short wire 320 is inserted into distal opening 183 of removable short wire tube 180.

Figure 9:
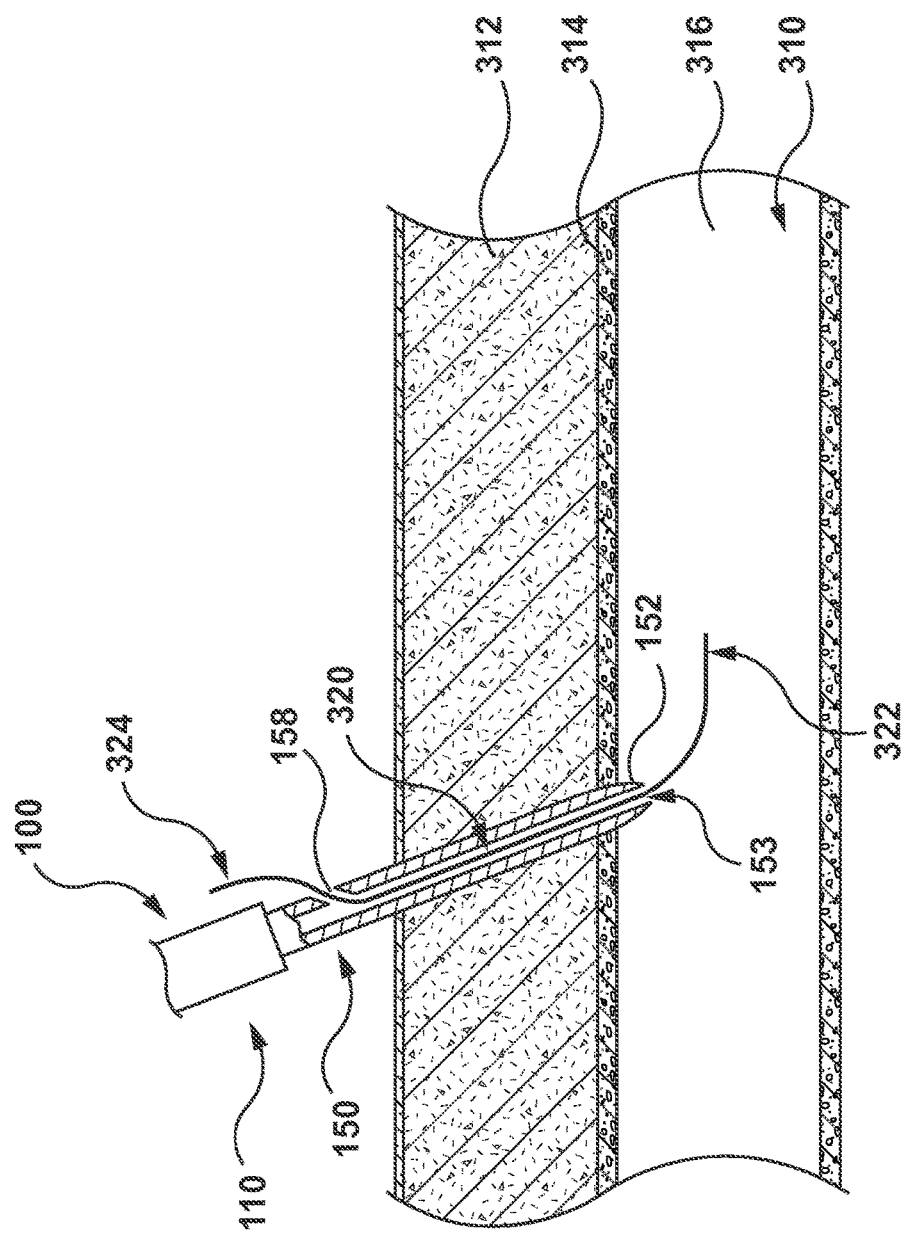

While short wire 320 is held in fixed position with respect to the patient by the clinician gripping the wire near the puncture site, guide catheter assembly 100 is advanced over the short wire 320 until short wire proximal end 324 exits through side exit port 158. To achieve this maneuver without losing control of short wire 320, the length of short wire 320 exposed from the patient must be at least as long as distance D1 from distal opening 153 to side exit port 158. E.g. see FIGS. 1 and 4. If obturator 170 of FIG. 2 is used, obturator 170 is positioned such that obturator distal end 171 is proximally adjacent to side exit port 158. Thus, as guide catheter assembly 100 is advanced over short wire 320, short wire proximal end 324 is deflected by angled surface 172 towards side exit port 158. Once short wire proximal end 324 extends from side port 158, the clinician may shift his/her grip on short wire 320 from near the puncture site to exposed short wire proximal end 324. Guide catheter assembly 100 is then advanced over the short wire 320 until dilator distal end 152 is disposed in lumen 316 of vessel 310, as shown in FIG. 9.

Figure 10:
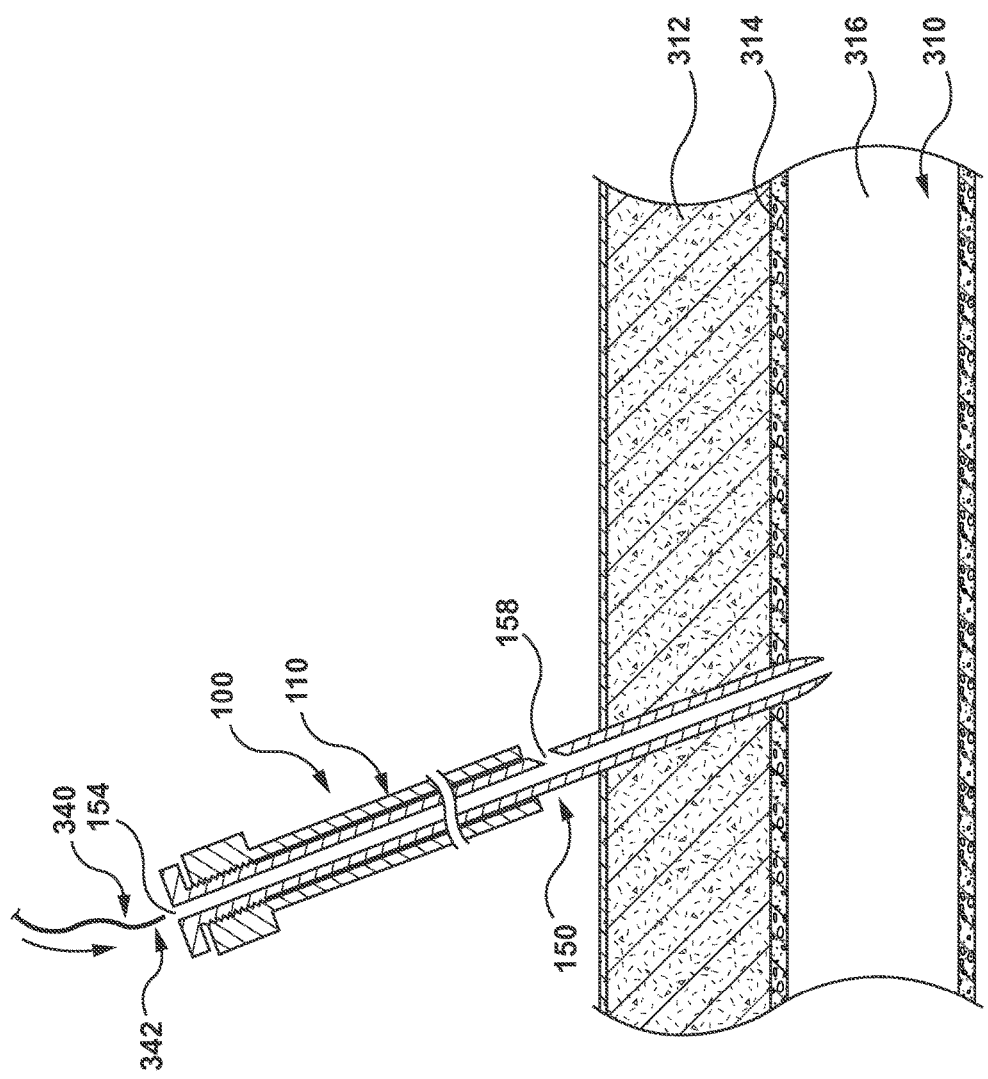

Short wire 320 is then removed from the patient and guide catheter assembly 100 by pulling on short wire proximal end 324. If the removable short wire tube 180 of FIG. 3 is used, it is also removed by pulling on proximal end 184 of removable short wire tube 180. This leaves guide catheter assembly 100 with distal end 152 of dilator 150 disposed in lumen 316 and guide catheter 110 disposed outside of the patient, as shown in FIG. 10. If the obturator 170 of FIG. 2 is used, it is also removed at this time.

A full-length angiography or procedural guidewire 340 is then loaded into guide catheter assembly 100 by inserting a distal end 342 of guidewire 340 into proximal opening 154 of dilator 150, as shown by the arrow in FIG. 10. Guidewire 340 is typically a nominal 0.035 or 0.038 inch diameter guidewire, as known to those skilled in the art. However, other guidewires may be used if appropriate for the particular procedure or access site. Guidewire 340 is advanced through guide catheter assembly 100 until distal end 342 of guidewire 340 exits distal opening 153 of dilator 150 such that distal end 342 of guidewire 340 is disposed in lumen 316 of vessel 310, as shown in FIG. 11.

Figure 11:
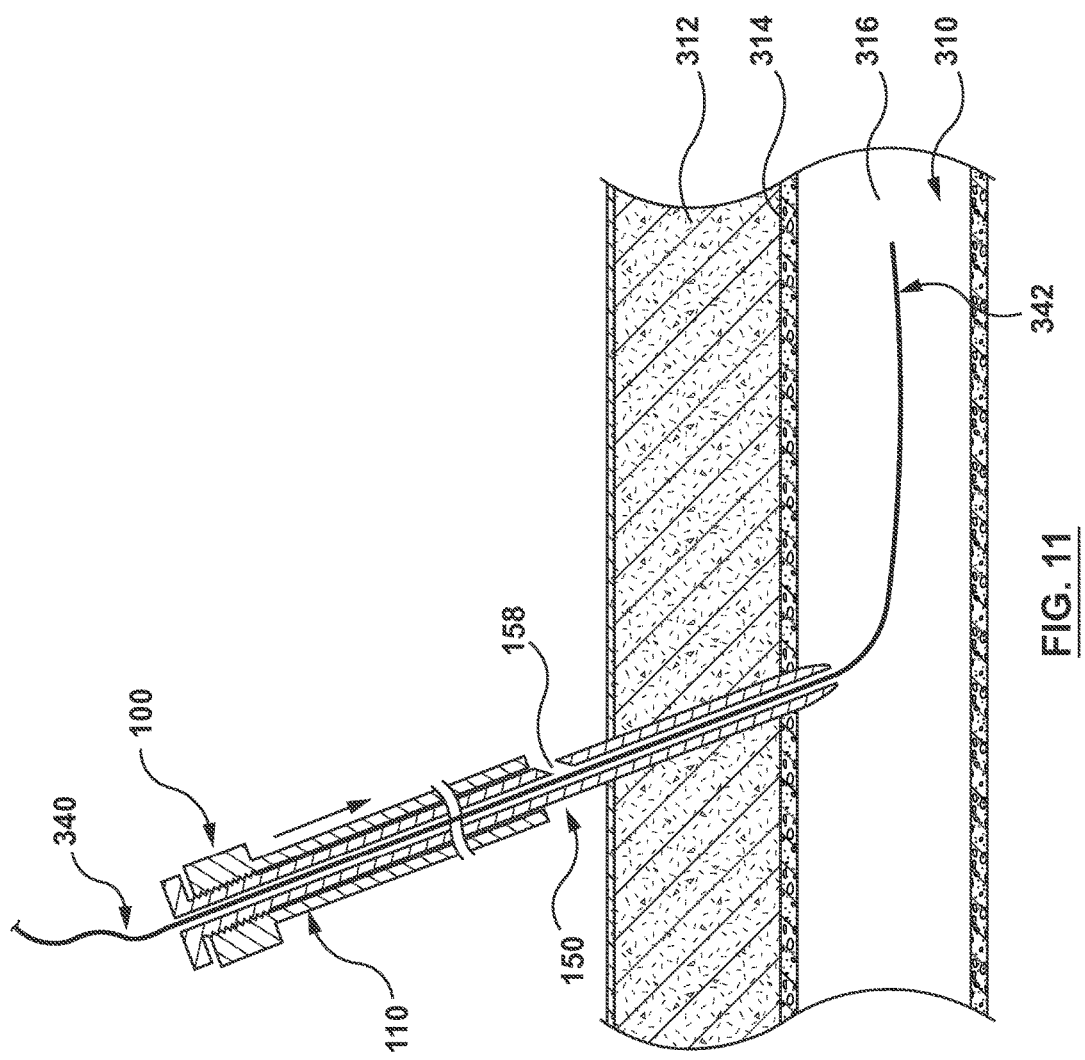
Figure 12:
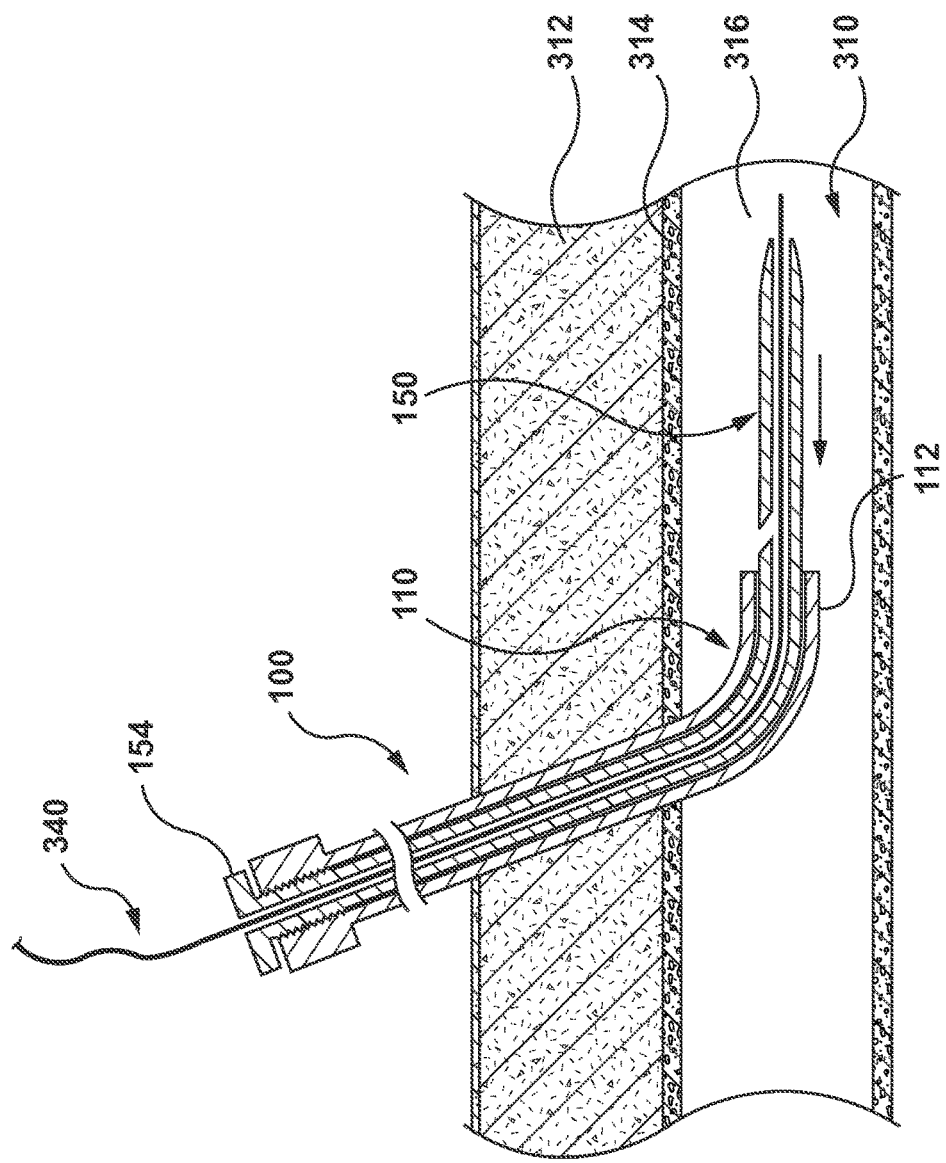

Guide catheter assembly 100 is then advanced over guidewire 340, as indicated by the arrow in FIG. 11 until distal end 112 of guide catheter 110 is disposed in lumen 316, as shown in FIG. 12. Dilator 150 may then be removed from guide catheter 110 by pulling on proximal end 154 of dilator 150 such that dilator 150 slides proximally through guide lumen 116, as indicated by the arrow in FIG. 12. With dilator 150 removed from guide catheter 110 as shown in FIG. 13, guide catheter 110 and guidewire 340 may be advanced to the desired site in the vasculature, as is known in the art. Optionally, guide catheter assembly 100 with dilator 150 disposed through guide catheter 210 can be advanced to the desired site in the vasculature using dilator 150 as a flexible leader. Thus, dilator 150 may be removed from guide catheter 110 before or after guide catheter assembly 100 reaches the desired site.

While the method described in FIGS. 5-13 has been described with respect to guide catheter assembly 100, and the additional features of FIGS. 2-3 have been described where appropriate, the guide catheter assembly 200 of FIG. 4 may also be used. When using the guide catheter assembly 200 of FIG. 4, the steps described with respect to FIGS. 5-9 are identical to the method described using guide catheter assembly 100. However, because dilator 250 of guide catheter assembly 200 does not include a lumen proximal of side exit port 258, guidewire 340 is not disposed through dilator 250 as described with respect to FIGS. 10-13. Instead, guide catheter assembly 200 is advanced with dilator 250 into lumen 316 of vessel 310. Then, using dilator 250 as a leader or acting as a guidewire, guide catheter assembly 200 with dilator 250 disposed through guide catheter 210 is advanced to the desired site in the vasculature. When guide catheter 210 reaches the desired site, dilator 250 is removed from within guide catheter 210. Alternatively, dilator 250 can be removed from guide catheter 210 and replaced with guidewire 340 before or after guide catheter assembly 200 reaches the desired site.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A guide catheter assembly comprising:
a dilator including a proximal end, a distal end, a dilator lumen extending from a distal opening at the distal end to a proximal opening at the proximal end, and a side exit port proximal of the distal opening, wherein the side exit port is in communication with the dilator lumen;
a guide catheter including a proximal end, a distal end, and a guide lumen extending between the proximal and distal ends of the guide catheter, wherein the dilator and the guide lumen are sized such that the dilator can pass through the guide lumen, and wherein the dilator and the guide catheter are sized such that with the proximal end of the dilator generally aligned along an axis with the proximal end of the guide catheter, the distal end of the dilator extends distally past the distal end of the guide catheter and the side exit port is disposed distal of the distal end of the guide catheter; and
a removable tube disposed through the side exit port and into the dilator lumen, wherein the removable tube includes a tube lumen with a smaller diameter than the dilator lumen, wherein the removable tube includes a proximal end and a distal end, wherein the proximal end is disposed adjacent to the side exit port when the distal end is disposed adjacent the distal opening of dilator lumen,
wherein the removable tube is removable from the dilator lumen through the side exit port.

2. The guide catheter assembly of claim 1, wherein the side exit port is sized to slidably receive a nominal 0.018-0.021 inch diameter guidewire therethrough.

3. The guide catheter assembly of claim 2, wherein the dilator lumen is sized to slidably receive a nominal 0.035 or 0.038 inch guidewire.

4. The guide catheter assembly of claim 1, further comprising a coupling mechanism for removably coupling the proximal end of the dilator to the proximal end of the guide catheter.

5. The guide catheter assembly of claim 1, wherein the guide catheter has a guide catheter length in the range of 90-150 cm, and wherein the dilator is longer than the guide catheter.

6. A method for accessing a vessel and delivering a guide catheter to a desired location in the vasculature of a patient, the method comprising the steps of:
inserting a needle through a wall of the vessel at an access site to create an access opening, wherein the needle includes a needle lumen;
inserting a first wire through the needle lumen and into the vessel, wherein the first wire has a first diameter;
removing the needle from the vessel over the first wire and leaving a distal end of the first wire in a lumen of the vessel with the first wire extending through the access opening;
inserting a proximal end of the first wire into a tube lumen of a removable tube disposed within a dilator lumen of a dilator of a guide catheter assembly, wherein the guide catheter assembly includes the dilator and a guide catheter having a guide lumen sized to receive the dilator therein;
guiding the proximal end of the first wire out of a side exit port of the dilator and a proximal end of the removable tube, wherein the side exit port is located proximal of the distal opening and distal of a distal end the guide catheter when a proximal end of the dilator and a proximal end of guide catheter are generally aligned along an axis, wherein the proximal end of the removable tube is disposed adjacent to the side exit port when a distal end of the removable tube is disposed adjacent to a distal opening of the dilator lumen;
advancing the guide catheter assembly over the first wire until a distal portion of the dilator enters the vessel;
removing the first wire from the vessel and the dilator by pulling the proximal end of the first wire such that the first wire retracts from the vessel, through the distal opening, and out of the side exit port;
removing the removable tube from the dilator lumen through the side exit port;
inserting a second guidewire into a proximal opening at a proximal end of the dilator, through the dilator lumen, and out of the distal opening into the vessel; and
advancing the guide catheter assembly over the second guidewire until a distal portion of the guide catheter is disposed in the lumen of the vessel.

7. The method of claim 6, further comprising the step of withdrawing the dilator through the guide lumen after the distal portion of the guide catheter is disposed in the vessel.

8. The method of claim 7, further comprising the step of advancing the guide catheter and the second guidewire to the desired location in the vasculature.

9. The method of claim 6, wherein the second guidewire has a second diameter larger than the first diameter of the first guidewire.

10. The method of claim 9, wherein the first guidewire has a nominal diameter of 0.018-0.021 inch and the second guidewire has a nominal diameter of 0.035 or 0.038 inch.

11. The method of claim 6, wherein the second guidewire has a nominal diameter of 0.035 or 0.038 inch and the dilator lumen is configured to receive the second guidewire when the removable tube is removed from the dilator lumen, and wherein the first wire has a nominal diameter of 0.018 to 0.021 inch and the tube lumen is configured to receive the first wire but cannot receive the second guidewire.

* * * * *